United States Patent [19]
Ludman et al.

[11] Patent Number: 5,805,283
[45] Date of Patent: Sep. 8, 1998

[54] INTERFEROMETRIC ENVIRONMENTAL MONITOR SYSTEM FOR MONITORING THE PRESENCE AND IDENTIFICATION OF POLLUTANTS

[75] Inventors: Jacques E. Ludman; Henri John Caulfield; David W. Watt; Jacques J. Ludman; Heidi L. Callahan, all of Hollis, N.H.

[73] Assignee: Northeast Photosciences, Inc., Hollis, N.H.

[21] Appl. No.: 667,982

[22] Filed: Jun. 19, 1996

[51] Int. Cl.$^6$ ............................................. G01B 9/02
[52] U.S. Cl. ............................................. 356/345; 356/361
[58] Field of Search ................................ 356/361, 358, 356/345

[56] References Cited

U.S. PATENT DOCUMENTS 5,416,587   5/1995   Riccobono et al. ............... 356/361

OTHER PUBLICATIONS

"Interferometric Atmospheric Refractive – Index Environmetal Monitor" Ludman et al, Applied Optics, Jun. 1995, pp. 3267–3273.

P.A. Vass, J.L. Van Genderen, Monitoring Environmental Pollution by Remote Sensing, Environmental Institute of Michigan 12th International Symposium on Remote Sensing of Environment, Manila, V1, Apr. 20–26 (1978), pp. 219–234.

J. Ludman, J. Riccobono, Index Interferometer, SPIE Opt. Info. Processing Systems, and Architecture. IV. vol. 1 1772 Jul. (1992), pp. 258–264.

T.S. Moss, Optical Properties of Semiconductors, Butterworth, London (1961), pp. 11–13.

G. Cavalcabo, L. Fiorina, M. Monguzzi, N. Pintus, E. Zanzottera, Development of LIDAR system or the diagnostics of combustion and emissions in a power plant, SPIE vol. 1717, Industrial, Municipal, and Medical Waste Incineration Diagnostics and Control, Berlin (1993), pp. 142–148.

E.S Ringler, V.P. Aneja, A ground based intercomparison of path integrated DOAS measurements and conventional point measurements of ambient trace gas concentrations, SPIE vol. 1715, Optical Methods in Atmospheric Chemistry, Berlin (1992), pp. 303–311.

D. Ritz, M. Hausmann, U. Platt, An improved Open Path Multi–Reflection Cell for the Measurement of NO2 and NO3, SPIE vol. 1715, Optical Methods in Atomspheric Chemistry, Berlin (1992), pp. 200–212.

J.L. Hudson, M.J. Thomas, J. Arello, J.R. Helvig, B.J. Fairless R.E. Carter, D.D. Lane, G.A. Marotz, Assessment of data intercomparability and data quality for multiple open–path FTIR systems, SPIE vol. 1717, Industrial, Municipal, and Medical Waste Incineration Diagnostics and Control, Berlin (1992), pp. 127–133.

(List continued on next page.)

*Primary Examiner*—Samuel A. Turner
*Attorney, Agent, or Firm*—Jacob N. Erlich; Jerry Cohen

[57] ABSTRACT

An interferometric environmental monitoring system having an active beam and a reference beam, each following an optical path, a detector system including a detector assembly, a pair of reflecting elements, the first reflecting element receiving the active beam and reflecting it, the second reflecting element receiving the reference beam and reflecting it. The reflected active and reflected reference beams are recombined into a recombined beam, which is directed to the detector assembly. The detector assembly monitors the central fringe of an interference pattern formed by interference when combining the active and the reference beams and providing an output signal related to the movement of the central fringe. The output signal being utilized to provide a signal representative of a condition which measurably affects the active beam.

20 Claims, 2 Drawing Sheets

OTHER PUBLICATIONS

P.R. Solomon, P.W. Morrison, M.S. Serio, R.M. Carangelo, J.R. Markham, S.C. Bates, J.E. Cosgrove, Fourier Transform Infrared Spectroscopy for processing and control, SPIE vol. 1717, Industrial, Municipal, and Medical Waste Incineration Diagnostics and Control, Berlin (1992), pp. 267–287.

M.J. Milton and P.T. Woods, Long–Path Methods for Remote Sensing of Pollutants in the Boundary Layer, vol. 1715, Optical Methods in Atmospheric Chemistry, Berlin (1992), pp. 312–321.

Excalibur Engineering, Fringe Locker III. 1260 North 200 East Suite 2, Logan, Utah 84321. R. Rallison, Jeff Brown, Jane Brown (1993).

INTERFEROMETRIC ENVIRONMENTAL MONITOR SYSTEM FOR MONITORING THE PRESENCE AND IDENTIFICATION OF POLLUTANTS

FIELD OF THE INVENTION

The present invention relates generally to interferometric measuring systems and, more particularly, to an interferometric system for monitoring the presence of and identifying environmental pollutants.

BACKGROUND OF THE INVENTION

There are a large variety of pollutants that enter the atmosphere and are either present at localized sites, or are pervasive. Examples of such pollutants include $CO_2$, $NO_2$, $SO_2$, and a large variety of hydrocarbons and other pollutants. These pollutants require monitoring and are currently being monitored in a variety of different ways.

An example of an environmental condition which calls for such monitoring of pollutants is in the remediation of waste sites, in which the release of local pollutants must be constantly monitored. However, in this age of pollutant control, many other such undesirable environmental conditions exist. Therefore, effective pollutant monitoring would be extremely desirable.

Past research by Jacques E. Ludman and Juanita Riccobono has led to the development of a laboratory instrument, the Index Interferometer as described in U.S. Pat. No. 5,416,587, to measure the index of refraction of laboratory samples with high accuracy. The key feature of the Index Interferometer is the use of intermediate spectral bandwidth (50 nm–100 nm) light as an integral part of the index measurement. Neither narrow spectral bandwidth (laser) or broad spectral bandwidth (white) light are effective. The purpose of the Index Interferometer is to determine the index and index variation of 1 mm–2 mm slices of material for research or quality control. However this laboratory instrument is not acceptable when it comes to very accurately monitoring index of refraction over long path lengths and to extend the use of such an interferometric devices into more hostile environments such as parking lots, industrial cleanup sites, industrial plants, etc.

Interferometers, in general, are used in the determination of optical path length changes to a small fraction of a micron with light or other forms of electromagnetic radiation. The measurement process involves counting a number of fringes which characterizes an optical path and uses the wavelength of the light to determine the thickness or optical path length. The potential of index interferometry has been recognized as, potentially, the most accurate way of determining the refractive index. The difficulty has always been in tracking a particular fringe (e.g. the zero order fringe) across a discontinuity. In the case of an optical path length measurement, it is necessary to identify a fringe from one surface, and identify the same fringe from another surface. The number of fringes between the frings e patterns is an exact measurement of the optical path difference between those two surfaces. Although the measurement procedure is relatively simple, difficulty occurs in identifying the same fringe from two different surfaces or locations. A common technique to identify a particular fringe is to use an auxiliary white (broad bandwidth) light source because a white light interference pattern is unambiguous. The central white light fringe corresponds to equal path lengths in the reference and test arms of the interferometer. Unfortunately, the white light pattern is only suitable for use as a reference with non-dispersive materials.

The Index Interferometer described above utilizes intermediate bandwidth light which leads to a pattern containing about 8 fringes. The visibility of the central fringe is substantially higher than that of the adjacent fringes, and it is also unambiguous. Since the bandwidth is significantly narrower than white light, the pattern is not significantly corrupted by a dispersive medium. This technique has permitted the measurement of the index of slices of material with an accuracy of 6 significant figures.

Past interferometric devices, such as the types described above, would not be able to distinguish among the various causes of changing optical path length, such as vibration, various pollutants, temperature changes, and moisture content of the air.

A classic problem with interferometry over long open paths is one of stability. The fringe patterns are in constant motion. Instabilities arise from several sources, but primarily from air turbulence and from vibration from a variety of sources. The laboratory solution, of course, is to avoid turbulence, to use very short interference arms, and to mount all parts of the interferometer on a very rigid optical table which is isolated from external vibrations. All of these approaches are impractical for in-the-field monitoring of pollutants.

Optical measurement techniques have also been proposed for the measurement of greenhouse gases such as chlorofluorocarbons, $CO_2$, and methane, volatile organics, $SO_2$, oxides of nitrogen, inorganic combustion products, toxic and radioactive metals, and others. Optical measurement of gas phase species concentration has generally been based on absorption, emission, or fluorescence spectroscopy using infrared or ultraviolet radiation. Although most techniques use bench-top instruments with gas sampling cells, a number of instruments have been applied to open path problems. These include differential absorption lidar (DIAL), differential optical absorption spectroscopy (DOAS), ultraviolet spectroscopy, and Fourier transform infrared systems (FTIR). The path lengths used in these applications range from the order of 5 meters for smokestack monitoring applications using FTIR to hundreds of meters for retroreflective DOAS and FTIR, to kilometers for lidar. The potential measurement accuracy of these instruments ranges from tens to thousands of ppb.

The application of these methods to continuous monitoring of pollutants, however, is limited by the presence of unknown species with absorption spectra that overlap those of the target species. Furthermore, in applications requiring the measurement of multiple species concentrations, or distinction among a few similar species with overlapping absorption spectra, such instruments may have trouble distinguishing between them. In addition, the measurements can be contaminated by spurious radiation emitted and scattered into the optical path by aerosols, particulates, and water droplets.

It is therefore an object of this invention to provide an interferometric system for accurate pollutant detection and identification.

It is a further object of this invention to provide an interferometric monitoring system capable of effective operation over long outdoor path lengths capable of compensating for vibration and turbulence.

It is still another object of this invention to provide an interferometric monitoring system which is inexpensive to manufacture.

It is still another object of this invention to provide an interferometric monitoring system which is substantially immune from incoherent sources of radiation.

It is still another object of this invention to provide an interferometric monitoring system which can produce very high data rates.

SUMMARY OF THE INVENTION

The present invention overcomes problems associated with past techniques for actively monitoring environmental pollutants. The key feature of the environmental monitoring system of this invention is the ability to maintain fringe stability in the presence of mechanical motion and atmospheric disturbance in order to effectively detect envronmental polutants. This is accomplished with the use of a movable mirror to compensate for any change in optical pathlength, thus keeping the fringe pattern absolutely stable. Stability is maintained by a "fringe locker", which detects any incipient motion of the fringe pattern and feeds back a voltage to control the mirror and lock the pattern. This results in a stable fringe pattern and a control voltage proportional to the variation in optical pathlength. The monitoring system of this invention, therefore, is capable of identifying and tracking a particular fringe despite unequally dispersive paths in the arms of the interferometer.

The preferred embodiment incorporates therein two beams of light. One beam, the reference beam, is in a controlled atmosphere and reflected off of a movable mirror. The other beam is the active beam, whose optical pathlength can change with the composition of the atmosphere or physical turbulence. The two beams are recombined to create a fringe pattern which moves with respect to the changing optical pathlength of the active beam. A photodetector system detects any of the fringe pattern movement and stabilizes the pattern with the aid of the moveable mirror. The voltage sent from the detector to the movable mirror is therefore proportional to the change in optical pathlength of the active beam.

For a better understanding of the present invention, together with other and further objects, reference is made to the following description taken in conjunction with the accompanying drawings, and in scope will be pointed out in the appended claims.

DETAILED DESCRIPTION OF THE PREFERRED EMBODIMENT

Figure 1:
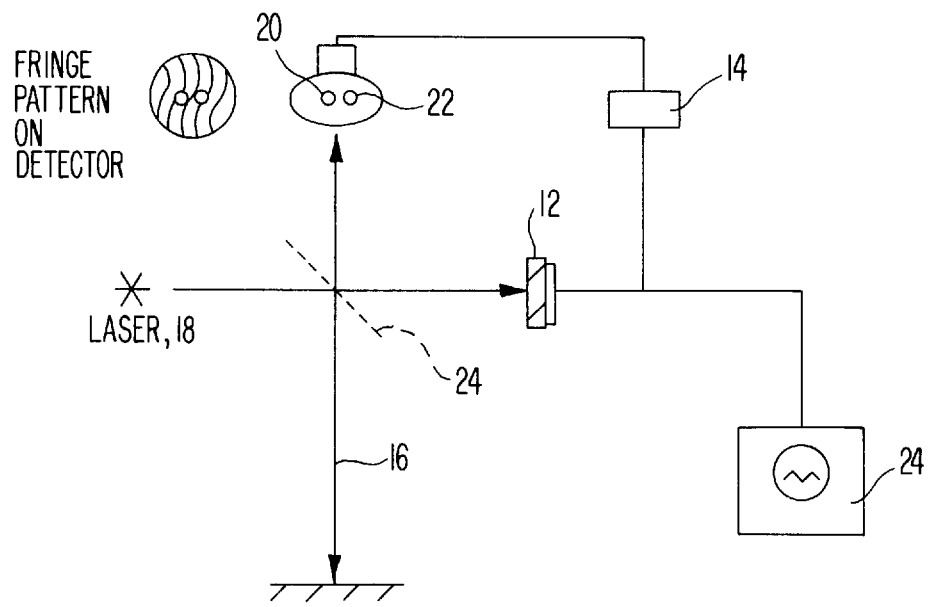
FIG. 1 is a schematic representation of an interferometric device utilized for describing the concept of the present invention.

In order to understand the basic concept of the interferometric environmental monitoring system of this invention, reference is first made to FIG. 1 of the drawings to describe the technique for stabilizing fringes in the presence of mechanical motion and atmospheric disturbance. This is accomplished with the use of a movable reflecting element in the form of mirror 12 to electronically compensate for any change in optical path length, thus keeping the fringe pattern absolutely stable. Mirror 12 is moved by means of any suitable actuators such as a piezoelectric crystal or an electromagnetic coil (not shown), and the amount of motion may be correlated with the voltage required to stabilize the pattern. Stability is maintained by a fringe locker 14 modified to provide an output signal indicative of movement of mirror 12. Fringe locker 12 detects any incipient motion of the fringe pattern and feeds back a voltage to control the mirror 12 and lock the pattern. This results in a stable fringe pattern and a control voltage proportional to the variation in optical path length 16. The fringe stabilization technique is standard practice in laboratory interferometry. The other components of interferometer 10 are a laser source 18, a pair of detectors 20 and 22, a beam splitter/combiner 24 and an oscilloscope 24. The unique relationship of these components within the present invention in detecting environmental pollutants will be described in greater detail below.

Figure 2:
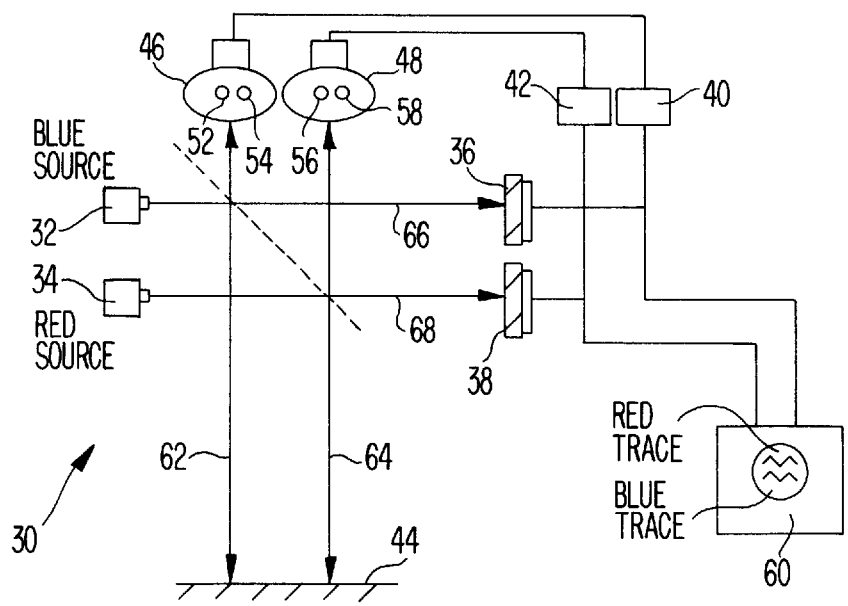
FIG. 2 is a schematic representation of a basic embodiment of the interferometric monitoring system of this invention.

A basic embodiment of the present invention is shown in FIG. 2 of the drawings. In this embodiment the interferometric environmental pollution monitor 30 of this invention is made up of the following components: at least two sources of electromagnetic radiation, preferably in the form of two sources 32 and 34 of filtered white light, one being a blue source and the other being a red source, respectively; a like number of movable reflective elements in the form of mirrors 36 and 38 and fringe lockers 40 and 42; a fixed reflective member or mirror 44; and detector assemblies 46 and 48, equal in number to the number of light sources, with each detector assembly 46 and 48 having a pair of photodetectors therein, 50, 52, and 54, 56; a beam splitter/combiner 58 and a signal monitoring device such as oscilloscope 60. More specifically, each of the detector assemblies 46 and 48 are made up of two small photodetectors a millimeter or two apart. Circuitry with response times in the kilohertz range detects and amplifies the intensity difference and sends a voltage signal to the drive mechanism of the movable mirrors 36 and 38, respectively, which moves the respective mirrors to hold the fringe pattern steady. The resultant output signal is passed onto oscilloscope 60 for analysis and can be further fed into a computer (not shown) for further analysis, if so desired.

In order to illustrate the principles of the interferometric environmental pollution monitoring system 30 of this invention, reference is still made to the embodiment of FIG. 2. In its simplest form, system 30 uses two sources 32 and 34 of filtered white light, one blue and one red. It should also be realized that the present invention is not limited to only two such sources, and a greater number may be used if so desired.

With the present invention it is necessary to locate the central, zero-order fringe from both the blue light and the red light on their respective photodetector assemblies 46 and 48 so that the relative path lengths in both the blue and the red can be effectively monitored. All of the optical path lengths are made substantially equal, with the active beams following optical paths 62 and 64, and the reference beams following optical paths 66 and 68. In use the fixed mirror 44 is located at an external source where pollutants are to be monitored and the remainder of the system 30, including movable mirrors 36 and 38, is preferably located in a building or other site removed from the fixed mirror 44. In order for optical paths 66, 68 to be equal to optical paths 62,64 a series of conventional folded mirrors (not shown) are optically aligned with the reference beams in optical paths 66 and 68. Thus, all optical paths from source to mirrors to detectors are substantially equal to each other.

Narrow bandwidth or laser sources are not suitable with the present invention since it would not be clear which fringe is being observed and it would not be clear whether one of the detectors has changed its lock to a different fringe. Consequently, intermediate bandwidth sources of, for example, approximately 50 nm could be used with the system of the present invention. As shown in FIG. 2 of the drawings, there are basically two systems operating independently, except that they share a common beam splitter/combiner 58 and a common long arm open air path and fixed mirror 44. The two movable mirrors 36 and 38 are co-mounted, but each responds to its own detector assembly 46 and 48, respectively, and color.

The environmental monitoring system 30 of this invention has its optical paths 62, 64 (active beams) passing through a long region of atmosphere to measure the index at a variety of wavelengths or over a continuous waveband. The system will sample at a rate, for example, of 1 KHz so that noise and turbulence effects can be easily filtered out. An intermediate bandwidth source is utilized so that the central fringe at each wavelength or over a continuous band of wavelengths can be identified readily and monitored. Small variations of the total path due to changes in temperature or moisture content will affect all wavelengths similarly. The variations due to temperature or moisture over a given bandwidth will have features such as gradual changes in index or as in the case of moisture, specific peaks, that will allow the determination of the effect as in fact due to a variation in temperature or moisture content. These effects will be slow drifts in the length of the active beams and can be easily monitored and nulled out. A key feature here is the use of an intermediate spectral bandwidth for the interferometric measurement.

Since the fringe lockers 40, 42 are chosen to have a response rate up to one KHz it is possible to sweep the spectrum of interest at rates approaching one KHz. As long as it is the central fringe being monitored, sweeping a bandwidth of a factor of 10 (0.5 micron to 5 microns, or 1 micron to ten microns) will lead to only relatively minor variations in index and within the one KHz response rate of the instrument. This response rate is a function of the fringe locker utilized. If necessary the system of this invention may be adapted with a higher response rate. The resulting measurement of this system is a measurement of the index as a function of wavelength with a repetition rate of, for example, 1 KHz. Any pollutant effects can be easily separated from other optical path length effects, because the effect as a function of wavelength and time of such pollutants is unique.

Figure 3:
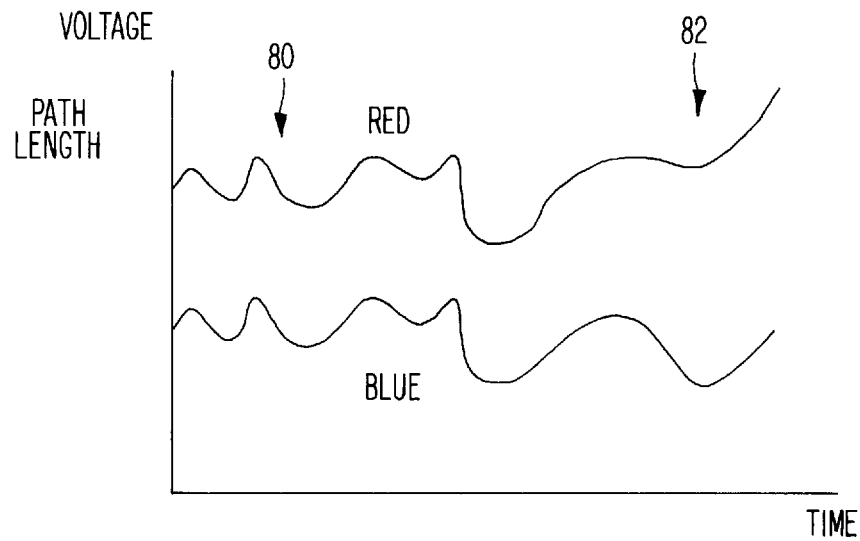
FIG. 3 is a graphic representation of changes in atmospheric composition.

Observation of the electronic signal corresponding to the movement of the mirrors 36 and 38 on a conventional dual-beam scope 60, provides several interesting bits of information as shown in the graph of FIG. 3 of the drawings. Physical motions such as brought about by vibration, turbulence, and temperature changes will lead to identical or very similar motions on both traces. On the other hand, changes in the nature of the atmosphere in the active beam optical paths 62 and 64 may have different effects at the two wavelengths. For example, moisture content changes and the addition or reduction of pollutants will have different effects at different wavelengths.

FIG. 3 shows a graphic simulation of a pair of two-color traces, somewhat exaggerated. The left-hand ends 80 of the traces (where the red and blue track each other) might represent higher frequency and some of the effects such as motion or vibration that are the same for both red and blue, while the right-hand ends 82 (where the red and blue diverge) show some dispersive effects, caused by changes in moisture content or pollutants. In practice one would not expect to see all these effects in the same trace, but the changes shown at the right end 82 would be changes that built up over a long period of time. The observation would require an oscilloscope 60 with memory capability so that traces could be compared over long periods of time. The use of a computer (not shown) to store, compare and analyze this information or data would also be desirable.

Referring once again to FIG. 2 of the drawings, in operation, the optical path may be distorted by introducing a pollutant to interfere with the active beams in paths 62 and 64. The fringe lockers 40 and 42 and movable mirrors 36 and 38 would completely electronically compensate for vibrations that would normally make outdoor measurements impossible due to rapid excursions in both directions. The voltage applied to the movable mirrors 36 and 38 may be displayed on an oscilloscope, voltmeter, or recorded for later analysis.

If one is monitoring an interference pattern from this invention having very long optical paths and also changing the wavelength as a function of time, the motion of the fringe being observed will change with wavelength unless the fringe being monitored is the central fringe. If one is monitoring the central fringe, then a change of wavelength will lead to an equal change in path lengths in all paths. If one is not observing the central fringe, but observing another fringe, a change in wavelength will change the number of wavelengths in one path compared to another. It is, therefore, essential with the present invention to be observing the central fringe since it does not move with changes in wavelength. Monitoring the central fringe has two major advantages; first there are not any spurious changes in path length due to a difference in the length of the optical paths and, second, the compensating mirrors 36 and 38 move only in response to changes in the index of refraction in the paths 62 and 64 of the active beams.

The interferometric environmental pollution monitoring system of this invention utilizes the spectral refractivity signatures of the component species of a gas mixture. Spectral absorption and spectral refractivity are not independent but rather, they are a Hilbert transform pair. Complete information about spectral absorption as a function of wavelength would permit the determination of spectral refractivity as a function of wavelength. Refractivity and absorption as a function of wavelength are therefore complementary, and their measurements are also complimentary. This is the Kramers-Kronig relation. Over a finite spectral band these effects are somewhat orthogonal and the spectral refractivity can add new information. By making optical path measurements at numerous wavelengths, a set of simultaneous relations between the concentrations of the component gases is obtained that can compliment the analysis of absorption spectra. Since refractivity measurements are immune to some of the noise sources that contaminate absorption measurement, refractivity spectra could greatly enhance noise rejection in open-path, finite band, absorption spectroscopy. In addition, the characteristic time for a full spectral scan by the present invention is about one millisecond, whereas competing pollution monitors generally have characteristic times greater than 10 milliseconds. Since the fringe locker response rates (easily increased) are on the order of one Khz, it is reasonable to do a spectral scan in times approaching one millisecond. In environmental remediation it is often important to follow the time evolution of pollutant concentration.

Figure 4:
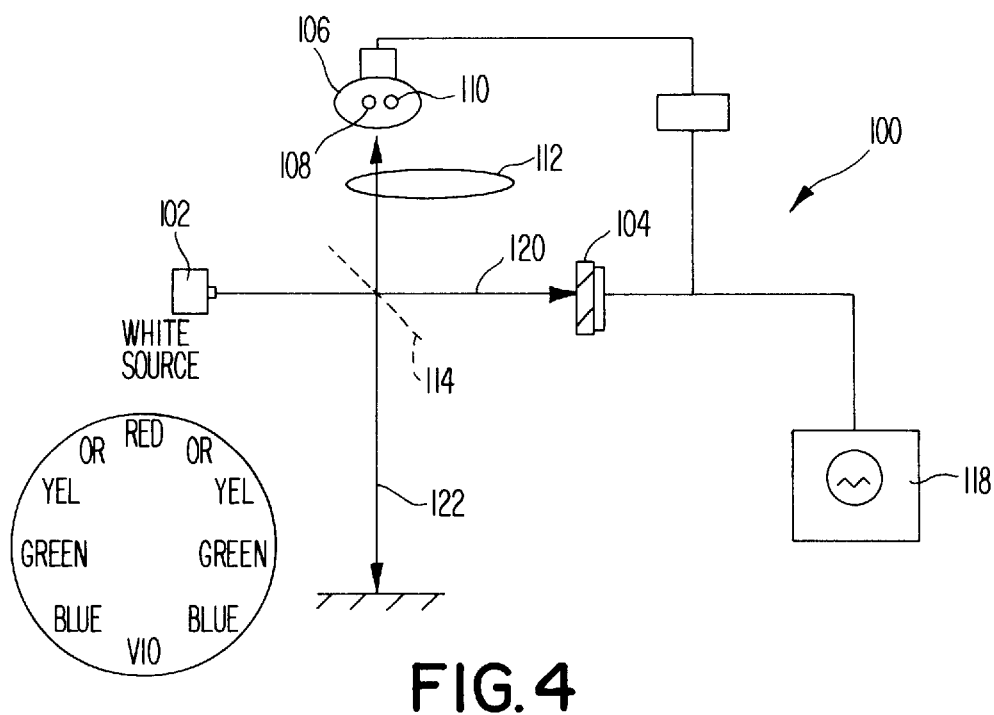
FIG. 4 is a schematic representation of the preferred embodiment of the interferometric monitoring system of this invention.

Reference is now made to FIG. 4 of the drawings which schematically illustrates the preferred embodiment of the interferometric environmental pollution monitoring system 100 of the present invention. In system 100, instead of two different colors propagating at the same time to two separate movable mirrors, there is one filtered white light source 102, one movable mirror 104, one detector assembly 106 having photodetectors 108 and 110 and a device to change the color such as a color wheel or circular variable filter (CVF) 112, along with beam splitter/combiner 114, fringe locker 116 and oscilloscope 118.

Although the color wheel or variable filter 112 is shown as being optically located between the detector assembly 106 and beam splitter 114, it could also be located adjacent source 102 before beam splitter 114. The CVF 112 can, more specifically, be a variable interference filter. When the CVF 112 is rotated, the transmitted color will have the appropriate bandwidth and change rapidly through the spectrum from red to violet and back to red again (or a similar wavelength spectrum in the infrared) as shown in the insert in FIG. 4.

The CVF 112 can easily be rotated at some moderate rate, of speed, such as one kilocycle, for example. This speed would be limited by the response time of the fringe locker 116 which will cause the optical path to change smoothly back and forth as the color changes from red to violet and back to red again, or across a spectral range in the infrared. The fringe locker 116 and the movable mirror 104 should have no difficulty locking on the same fringe throughout this process.

It is important that the fringe locker 116 be locked on the central fringe, corresponding to equal path lengths between the reference beam along optical path 120 and the active beam 122 so that the motion of movable mirror 104 corresponds to actual changes in the optical path length due to the dispersion of an intervening medium, such as, for example, a pollutant in optical path 122. A series of reflectors(not shown) can be utilized in conjunction with the reference beam in order to fold the optical path 120 and make it substantially equal to optical path 122. Fringes other than the central fringe move with wavelength change as well as with optical path length change. The signal from the spectrum scanning system as described will be repetitive at a rate of, for example, one KHz. A convenient method for display will be an oscilloscope 18 triggered at the same rate. In addition a computer can be utilized with the present invention in order to analyze or store data with respect to pollutants detected with the present invention.

Utilizing the environmental pollution monitoring system 30 of FIG. 2, an experiment was set up with optical path lengths of approximately ½ meters in length. An impurity such as O$_2$ was introduced into the active arm and the motion of the interference fringe pattern from a monochromatic source was observed as the composition of the gas slowly changed from air to 100% pollutant (e.g. O$_2$). The experiment was then repeated but with fringe lockers 40,42 locking the pattern in place and controlling the movable mirrors in the reference arm. Monitoring the voltage on the mirrors gave a direct indication of the distance the movable mirrors were displaced and the corresponding change in the optical path. Qualitative observations were then made of the effects of simulated air turbulence (bursts of compressed air, table vibrations, shaking and the like) to determine whether the electronic signals were suitable for monitoring optical path changes. The fringe pattern with no electronic compensation simply blurred and became unreadable with either simulated air turbulence or table vibrations. With the electronic compensation from the fringe locker, the fringe pattern remained stable, and the optical path length changes were easily monitored with the electronic signals.

The experimental set up was then modified to duplicate the system as shown in FIG. 4 except no color wheel or CVF 112 was included and the preliminary laboratory light source was a HeNe laser at 6328 A. A fringe pattern was then established. The optical path 122 of the active arm of the system traveled through a 6 cm tube to which pollutants could be added in a controlled manner. The optical path 120 of the reference arm had a movable mirror 104 mounted to a piezoelectric crystal. The reference arm was actually folded to conserve space and double the sensitivity or, more specifically, the reference beam reflected from the movable mirror, then to a fixed mirror and back to the movable mirror and finally to the beam splittercombiner, recombining with the active beam to form fringes on detector assembly 106. The voltage output of the movable mirror 104 was monitored on oscilloscope 118.

While filling the experimental pollutant tube with oxygen, the voltage change from the movable mirror 104 was recorded. Since this output can be used to find the change in optical path length, it is possible to determine the index of the pollutant. As stated, the sensitivity of the system was doubled by folding the reference arm so that motion of the movable mirror 104 by $\Delta$ x changed the optical path by 2 $\Delta$ x.

Because air and oxygen have almost the same index and because the path was only 6 cm, the optical path difference was small, about 3.8±0.1 fringes, or 0.9 wavelengths. In this experiment, the fringe shift was measured with a 3% experimental accuracy and obtained the listed index value of O$_2$ at one atmosphere to within experimental accuracy.

These experiments proved that it is possible to convert an optical signal into a much more convenient electronic signal suitable for monitoring variations in optical path length over a long path. This appears to be particularly useful for the interferometric environmental pollution monitoring system of this invention where rapidly varying (1 kHz) wavelength scanning will be utilized. The fringe pattern will be changing in color, intensity, and fringe separation (because of the wavelength change) and added to this will be the changes due to turbulence, vibration, temperature, and humidity. Superimposed on this will be the desired information, the variation of the index as a function of wavelength due to the introduction of impurity or pollutant gases into the atmosphere. The processing for the electronic signal is not excessively demanding. Frequency filtering can remove or process the bulk of the unwanted information or noise. The unoptimized experiment further showed a remarkable tolerance for induced vibration and turbulence estimated at 10–400 Hz. Disturbances which destroy an uncompensated fringe pattern were easily stabilized producing an interpretable scope trace.

The preliminary tests with a 6 cm chamber gave detectable index changes of 0.1 fringe corresponding to 3 parts per 100 or 3% pollutant. For a 1 km path, this corresponds to 6 ppm detectability. Pollutants which have larger pollutant-air index differences than oxygen will be detectable at correspondingly lower concentrations (ppbs).

The monitoring system 100 of the present invention compares air (index $n_{air}$) in optical path 120 of the system with some other gas (index $n_G$) in the open optical path 122. Both paths have the same, long path length Thus the OPD between the paths is l.

$$OPD_G = l|n_A - n_G|. \tag{1}$$

The gas itself is mostly air with a little pollutant. Suppose we had a pure 1-atm pollutant in one arm and pure 1-atm air in the other. Then we would have $$OPD_P = l|n_A - n_P|. \tag{2}$$

Normally $|n_A-n_G|$ is of the order of $10^{-4}$, so a good figure of merit of a pollutant's index detectability is $$\alpha_p = 10^4 |n_A - nP|, \quad (3)$$

so $$OPD_P = 10^{-4} \, l \, \alpha p. \quad (4)$$

In practice, there will be only a small amount of pollutant (e), where e<<1. Thus the measured OPD is $$OPD_{Mixture} = (1 - \epsilon)OPD_{Air} + (\epsilon)OPD_{Pollutant} \quad (5)$$
$$= \epsilon OPD_p \quad (6)$$
$$= \epsilon l \alpha_p (10^{-4}); \quad (7)$$

then $$\epsilon = (OPD)_M / (l\alpha_p \times 10^{-4}). \quad (8)$$

If the minimum detectable $(OPD)_M$ is $\frac{1}{100}$, then the minimum detectable concentration of that pollutant is $$\epsilon_{min} = (100\lambda/\alpha_p l). \quad (9)$$

Consider $\lambda = 0.5 \times 10^{-6}$ m (green) and $l = 10^3$ m. Then, $$e_{min} = (0.5 \times 10^{-1})/\alpha_p = 50 \, ppb/\alpha_p. \quad (10)$$

TABLE 1

Minimum Detectable Atmospheric Pollutant concentrations

| Pollutant | $\alpha_p$ | $\epsilon_{min}$ (ppb) |
|---|---|---|
| Air | 0.00 | |
| $O_2$ | 0.22 | 231 |
| $O_3$ | 2.23 | 22 |
| $SO_2$ | 3.67 | 13 |
| CO | 0.42 | 117 |
| $H_2O$ | 0.40 | 123 |
| HCl | 1.54 | 32 |
| $N_2O$ | 2.16 | 23 |
| Chloroform | 11.51 | 4 |

Table 1 shows $\alpha_p$ for various pollutants at 0.57–0.59 μm wavelengths. The detectability index ($\alpha_p$) varies tremendously among possible pollutants. Fortunately, some of the most important pollutants have the highest detectability. The minimum detectability $\epsilon_{min}$ listed in Table 1 is for a 1-km path and $\lambda = 0.5$ μm visible light. It is given in integrated or average ppb over the 1-km path. Indices were taken at 760 mm and 0° C.

The best use for the environmental monitoring system of this invention appears to be for detecting concentrations of a pollutant which is known a priori e.g. leakage from storage tanks or known waste site remediation or industrial plant perimeter monitoring. These are pure quantification problems uncomplicated by identification. On the other hand, the pollutants will have distinct spectral refractivity signatures near their unique absorption signatures, allowing identification in some instances.

In addition the system can be used to measure refractive index across an area that is not otherwise accessible. The test path of course can be folded so as to either traverse over an area such as a waste site or can be set up as a perimeter detector to encircle an area or building to monitor possible leakage or other emissions. Because of the one millisecond resolution, it is ideal for measuring the time evolution of pollution events.

Although the invention has been described with reference to particular embodiments, it will be understood that this invention is also capable of further and other embodiments within the spirit and scope of the appended claims.

What is claimed is:

1. An interferometric environmental monitoring system comprising:
   means for providing a beam of electromagnetic radiation along an optical path;
   means optically interposed within said optical path for dividing said beam into an active beam and a reference beam, each following an optical path;
   a detector system including a detector assembly;
   first reflecting means for receiving said active beam and reflecting said active beam;
   second reflecting means for receiving said reference beam and reflecting said reference beam;
   means optically aligned with said reflected active and reflected reference beams for recombining said beams into a recombined beam, said recombining means directing said recombined beam to said detector assembly;
   said detector assembly including means for monitoring the central fringe of an interference pattern formed by interference when combining said active and said reference beams, said detector system providing an output signal related to the movement of said central fringe;
   means interposed between said beam providing means and said detector assembly for continuously, preselectively varying the wavelength of said active and reference beams; and
   means operably connected to said detector system for receiving said output signal and providing a signal representative of a condition which measurably affects said active beam.

2. An interferometric environmental monitoring system as defined in claim 1 wherein said second reflecting means comprises a movable reflecting element.

3. An interferometric environmental monitoring system as defined in claim 2 wherein said detector system comprises means for providing said output to move said movable reflecting element, thereby maintaining said optical paths of said active and said reference beams substantially equal in length in order to lock said central fringe.

4. An interferometric environmental monitoring system as defined in claim 1 wherein said first reflecting means is in a location where said environment is to be monitored.

5. An interferometric environmental monitoring system as defined in claim 3 wherein said first reflecting means is in a location where said environment is to be monitored.

6. An interferometric environmental monitoring system as defined in claim 3 wherein said beam dividing means and said beam recombining means are incorporated in the same component.

7. An interferometric environmental monitoring system as defined in claim 3 wherein said monitoring means comprises a pair of photodetectors for receiving said recombined beams.

8. An interferometric environmental monitoring system as defined in claim 1 wherein said means for varying said wavelength of said active and reference beams comprises a variable filter.

9. An interferometric environmental monitoring system as defined in claim 1 wherein said means for varying said wavelength of said active and reference beams comprises a color wheel.

10. An interferometric environmental monitoring system as defined in claim 1 wherein said means for varying said wavelength of said active and reference beams is optically interposed between said beam dividing means and said detector assembly.

11. An interferometric environmental monitoring system comprising:
- means for providing at least two separate beams of electromagnetic radiation along respective optical paths, each of said beams being of a different wavelength;
- means optically interposed within said optical paths for dividing each of said beams into respective active beams and reference beams, each of said beams following an optical path;
- a detector system including at least two detector assemblies;
- first reflecting means for receiving said active beams and reflecting each of said active beams;
- second reflecting means for receiving said reference beams and reflecting each of said reference beams;
- means optically aligned with each of said reflected active and reflected reference beams for recombining each of said reflected active and reflected reference beams into respective recombined beams, said recombining means directing each of said respective recombined beams to a respective one of said detector assemblies;
- each of said detector assemblies further including means for monitoring the central fringe of an interference pattern formed by interference when combining each of said respective active and said reference beams, said detector system providing output signals related to the movement of said central fringe; and
- means operably connected to said detector system for receiving said output signals and providing an output representative of a condition which measurably affects said active beams.

12. An interferometric environmental monitoring system as defined in claim 11 wherein said second reflecting means comprises a pair of movable reflecting elements.

13. An interferometric environmental monitoring system as defined in claim 12 wherein said detector system comprises means for providing said output signals to move said movable reflecting elements, thereby maintaining said optical paths of said active and said reference beams substantially equal in length in order to lock said central fringe.

14. An interferometric environmental monitoring system as defined in claim 11 wherein said first reflecting means is in a location where said environment is to be monitored.

15. An interferometric environmental monitoring system as defined in claim 13 wherein said first reflecting means is in a location where said environment is to be monitored.

16. An interferometric environmental monitoring system as defined in claim 13 wherein said beam dividing means and said beam recombining means are incorporated in the same component.

17. An interferometric environmental monitoring system as defined in claim 13 wherein said monitoring means comprises a pair of photodetectors for receiving said recombined beams.

18. An interferometric environmental monitoring system as defined in claim 1 wherein said electromagnetic radiation emanates from an intermediate bandwdth source of light.

19. An interferometric environmental monitoring system as defined in claim 11 wherein said electromagnetic radiation emanates from an intermediate bandwdth source of light.

20. A method of monoritoring the environment, comprising the steps of:
- providing a beam of electromagnetic radiation;
- dividing said beam into an active beam and a reference beam, each following an optical path;
- receiving said active beam and reflecting said active beam;
- receiving said reference beam and reflecting said reference beam;
- recombining said beams into a recombined beam, said recombining means directing said recombined beam to said detectiong assembly;
- monitoring the central fringe of an interference pattern formed by interference when combining said active and said reference beams, and providing an output signal related to the movement of said central fringe;
- continuously, preselectively varying the wavelength of said active and reference beams; and
- receiving said output signal and providing a signal representative of a condition which measurably affects said active beam.

* * * * *